US007002685B2

(12) United States Patent
Wang

(10) Patent No.: US 7,002,685 B2
(45) Date of Patent: Feb. 21, 2006

(54) SYSTEM FOR MEASURING OF BOTH CIRCULAR AND LINEAR BIREFRINGENCE

(75) Inventor: Baoliang Wang, Beaverton, OR (US)

(73) Assignee: Hinds Instruments, INC, Hillsboro, OR (US)

( * ) Notice: Subject to any disclaimer, the term of this patent is extended or adjusted under 35 U.S.C. 154(b) by 201 days.

(21) Appl. No.: 10/240,290

(22) PCT Filed: Mar. 23, 2002

(86) PCT No.: PCT/US02/09384

§ 371 (c)(1),
(2), (4) Date: Apr. 29, 2003

(87) PCT Pub. No.: WO01/73385

PCT Pub. Date: Oct. 4, 2001

(65) Prior Publication Data

US 2003/0179375 A1 Sep. 25, 2003

Related U.S. Application Data

(60) Provisional application No. 60/193,652, filed on Mar. 31, 2000.

(51) Int. Cl.
*G01J 4/00* (2006.01)
(52) U.S. Cl. .................................................. 356/364
(58) Field of Classification Search ........ 356/364–368, 356/450, 453, 491; 250/225, 227.17, 252.1
See application file for complete search history.

(56) References Cited

U.S. PATENT DOCUMENTS

| 4,306,809 A | * | 12/1981 | Azzam ........................ 356/368 |
| 4,668,086 A | | 5/1987 | Redner |
| 4,801,798 A | * | 1/1989 | Lange ......................... 250/225 |
| 4,850,710 A | | 7/1989 | Mochida et al. |
| 5,268,305 A | * | 12/1993 | Ribi et al. .................... 436/501 |
| 5,319,194 A | * | 6/1994 | Yoshizumi et al. ......... 250/225 |
| 5,457,536 A | * | 10/1995 | Kornfield et al. ........... 356/366 |
| 5,521,705 A | | 5/1996 | Oldenbourg et al. |
| 5,536,936 A | * | 7/1996 | Drevillon et al. ........... 250/226 |
| 5,825,492 A | * | 10/1998 | Mason ........................ 356/491 |
| 5,956,146 A | | 9/1999 | Nakagawa |
| 5,956,147 A | * | 9/1999 | Jellison et al. .............. 356/369 |
| 6,473,181 B1 | | 10/2002 | Oakberg |

* cited by examiner

*Primary Examiner*—Layla G. Lauchman
(74) *Attorney, Agent, or Firm*—Ipsolon LLP

(57) ABSTRACT

A system and method for precisely measuring low-level linear and circular birefringence properties (retardance and direction) of optical materials (26). The system incorporates a photoelastic modulator (24) for modulating polarized light that is then directed through a sample (26). The beam ("Bi") propagating from the sample is separated into two parts, with one part ("B1") having a polarization direction different than the polarization direction of the other beam part ("B2"). These separate beam parts are then processed as distinct channels. Detection mechanisms (32, 50) associated with each channel detect the time varying light intensity corresponding to each of the two parts of the beam. This information is combined for calculating a precise measure of the linear and/or circular retardance induced by the sample, as well as the sample's fast axis orientation and direction of circular retardance.

16 Claims, 7 Drawing Sheets

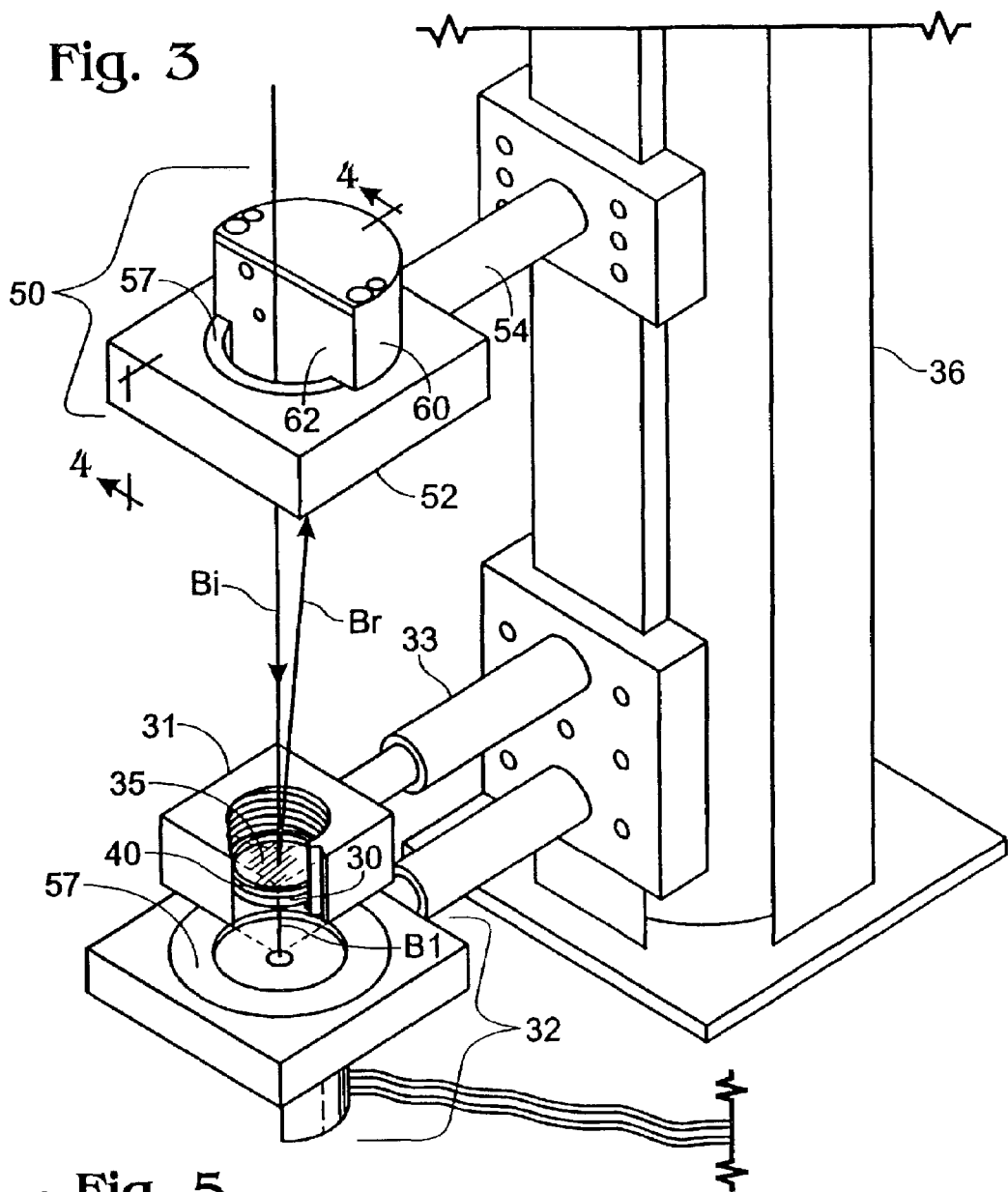
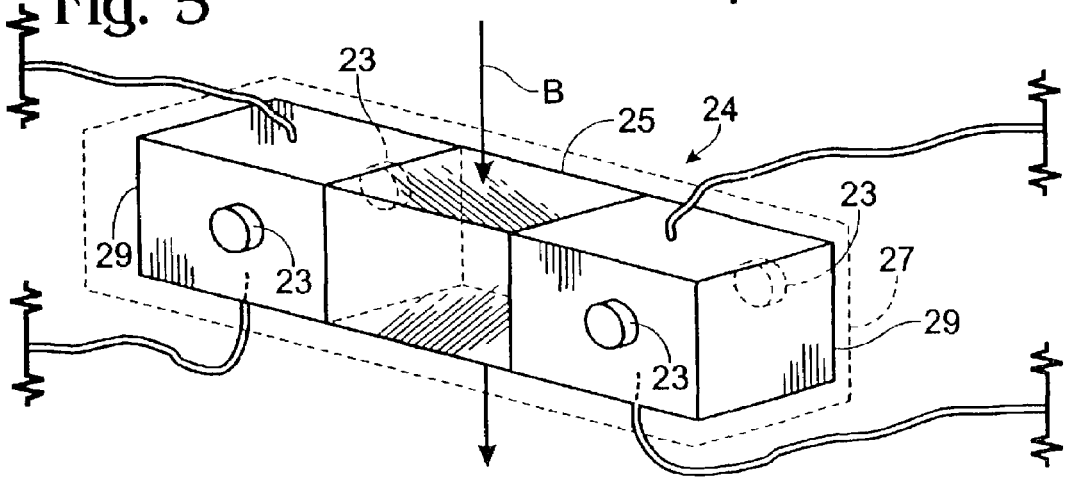

CALIBRATION OF FUSED SILICA PEM

CORRECTION FACTOR vs. WAVELENGTH FOR BIREFRINGENCE MEASURED AT 633 nm

SYSTEM FOR MEASURING OF BOTH CIRCULAR AND LINEAR BIREFRINGENCE

TECHNICAL FIELD

This invention relates to a system for measuring both linear birefringence and circular birefringence (magnitude and angle) in a transparent sample.

BACKGROUND AND SUMMARY OF THE INVENTION

Many important optical materials exhibit birefringence. Birefringence means that different polarizations of light travel at different speeds through the material. These different polarizations are most often considered as two components of the polarized light, one being orthogonal to the other.

Birefringence is an intrinsic property of many optical materials, and may also be induced by external forces or fields. Retardation or retardance represents the integrated effect of birefringence acting along the path of a light beam traversing the sample. If the incident light beam is linearly polarized, two orthogonal components of the polarized light will exit a linearly birefringent sample with a phase difference, called the retardance. If the incident light beam is circularly polarized, two orthogonal components of the polarized light will exit a circularly birefringent sample with a phase difference, called the retardance. The fundamental unit of retardance is length, such as nanometers (nm). It is frequently convenient to express retardance in units of phase angle (waves, radians, or degrees), which is proportional to the retardance (nm) divided by the wavelength of the light (nm). An "average" birefringence for a sample is sometimes computed by dividing the measured retardation magnitude by the thickness of the sample.

The need for precise measurement of birefringence properties has become increasingly important in a number of technical applications. For instance, it is important to specify and control the residual linear birefringence (hence, the attendant induced retardance) in optical elements used in high precision instruments employed in semiconductor and other industries. The optics industry thus has a need for a highly sensitive instrument for measuring linear birefringence in optical components. This need has been largely unmet, especially with respect to measurements of low levels of retardance.

Linearly polarized light may also be characterized as the superposition of two components of circularly polarized light (right-hand and left-hand senses) having identical amplitude and frequency or wavelength. The relative phases of the two circular polarization components determines the polarization plane. The plane of polarization will be rotated in instances where the refractive indices of a sample are slightly different for the two senses of circular polarization. This rotation of the polarization plane is referred to as optical rotation. Optical rotation is also referred to as circular birefringence because it relates to the phase shifting of the circular polarization components that is attributable to the different refractive indices.

If linearly polarized light passes through chiral media, such as, for example a solution of chiral molecules, the polarization of the incident light will be rotated. This circular birefringence (or optical rotation) is often referred to as natural optical rotation to distinguish it from Faraday rotation in a magnetic field. The extent of optical rotation, therefore, is indicative of the molecular structure (the chirality) of such media. Thus, the precise detection and analysis of the optical rotation, or circular birefringence, imparted by sample of chiral medial is useful for analytical chemistry, pharmaceutical, and biological industries.

The complete description of each linear and circular birefringence requires two parameters. Both linear and circular birefringence of a sample along a given optical path require specifying the magnitude of the birefringence, or the amount of integrated phase retardation along the given optical path length. For linear birefringence, it is also required to specify the fast axis of the sample. The two orthogonal polarization components described above are parallel to two orthogonal axes, which are determined by the sample and are called the "fast axis" and the "slow axis." The fast axis is the axis of the material that aligns with the faster moving component of the polarized light through the sample. For circular birefringence, the sense of optical rotation, in terms of clockwise or anticlockwise, should be specified. Therefore, a complete description of the linear and circular birefringence of a sample along a given optical path requires specifying both the magnitude of the birefringence, the relative angular orientation of the fast (or slow) axis, and the rotational direction (for circular birefringence).

The present invention is directed to a practical system and method for precisely measuring low-level linear and circular birefringence properties of optical materials. The retardance magnitude and orientation of the fast axis are precisely calculated, as well as the rotational direction. The system permits multiple measurements to be taken across the area of a sample to detect and graphically display variations in the retardance across the sample area.

In a preferred embodiment, the system incorporates a photoelastic modulator for modulating polarized light that is then directed through a sample. The beam propagating from the sample is separated into two parts. These separate beam parts are then analyzed at different polarization directions, detected, and processed as distinct channels. The detection mechanisms associated with each channel detect the light intensity corresponding to each of the two parts of the beam. This information is employed in an algorithm for calculating a precise, unambiguous measure of the retardance induced by the sample and the orientation of the fast axis.

As one aspect of this invention, the system includes a beam-splitting member and detector arrangement that permits splitting the beam into two parts with minimal contribution to the retardance induced in the beam. Moreover, the presence of any residual birefringence in the optical system (such as may reside as static birefringence in the photoelastic modulator or in any of the optical components of the system) is accounted for in a number of ways. For example, certain of the system components are arranged or mounted to minimize the chance that strain-induced birefringence may be imparted into the element. A reliable calibration technique is also provided.

The system permits the low-level linear and circular birefringence measurements to be taken at any of a plurality of locations across the area of the sample. The measurements are compiled in a data file and graphically displayed for quick analysis.

In one embodiment of the invention, the optical components of the system are arranged to measure the birefringence properties of a sample that is reflectively coated on one side, thereby permitting measurement of birefringence properties even though the sample is not completely light transmissive.

Other advantages and features of the present invention will become clear upon study of the following portion of this specification and drawings.

BRIEF DESCRIPTION OF DRAWINGS

FIG. 3 is a perspective view of detection and beam-splitting components of the system.

FIG. 5 is a perspective view of the primary components of a photoelastic modulator that is incorporated in the present system.

FIG. 7 is a diagram of an alternative embodiment of the present invention.

BEST MODES FOR CARRYING OUT THE INVENTION

Linear Retardance Measurement

Figure 1:
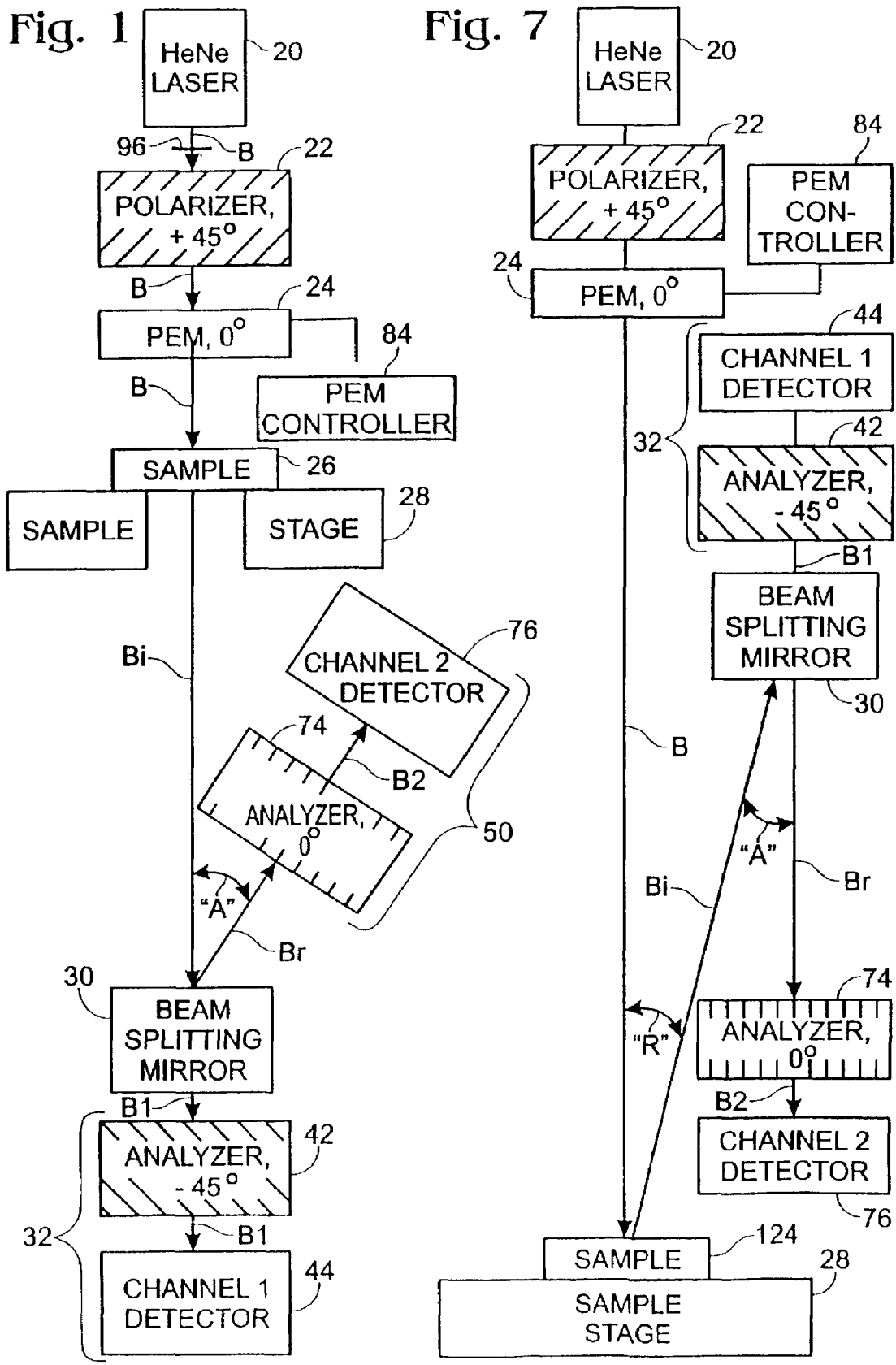
FIG. 1 is a diagram of a preferred embodiment of the present system showing the preferred arrangement of the optical components.

The diagram of FIG. 1 depicts the primary optical components of a system made in accordance with the present invention. The components include a HeNe laser as a light source 20 that has a wavelength of 632.8 nanometers (nm). The beam "B" emanating from the source has a cross sectional area or "spot size" of approximately 1 millimeter (mm).

The source light beam "B" is directed to be incident on a polarizer 22 that is oriented with its polarization direction at +45° relative to a baseline axis. A high-extinction polarizer, such as a Glan-Thompson calcite polarizer, is preferred. It is also preferred that the polarizer 22 be secured in a precision, graduated rotator.

The polarized light from the polarizer 22 is incident on the optical element 25 of a photoelastic modulator 24 (FIGS. 1 and 5). In a preferred embodiment, the photoelastic modulator (hereafter referred to as a "PEM") is one manufactured by Hinds Instruments, Inc., of Hillsboro, Oreg., as a low birefringence version of Model PEM-90 I/FS50. It is noteworthy here that although a PEM is preferred, one could substitute other mechanisms for modulating the polarization of the source light.

The PEM has its birefringent axis oriented at 0° and is controlled by a controller 84 that imparts an oscillating birefringence to the optical element 25, preferably at a nominal frequency of 50 kHz. In this regard, the controller 84 drives two quartz transducers 29 between which the optical element 25 is bonded with an adhesive.

The oscillating birefringence of the PEM introduces a time-varying phase difference between the orthogonal components of the polarized light that propagates through the PEM. At any instant in time, the phase difference is the retardation introduced by the PEM. The retardation is measurable in units of length, such as nanometers. The PEM is adjustable to allow one to vary the amplitude of the retardation introduced by the PEM. In the case at hand, the retardation amplitude is selected to be 0.383 waves (2.405 radians).

The beam of light propagating from the PEM is directed through the transparent sample 26. The sample is supported in the path of the beam by a sample stage 28 that is controllable for moving the sample in a translational sense along orthogonal (X and Y) axes. The stage may be any one of a number of conventional designs such as manufactured by THK Co. Ltd., of Tokyo, Japan as model KR2602 A-250. As will become clear, the motion controllers of the sample stage 28 are driven to enable scanning the sample 26 with the beam to arrive at a plurality of retardation and orientation measurements across the area of the sample.

The sample 26 will induce retardance into the beam that passes through it. It is this retardance value that is determined in accordance with the processing provided by the present invention, as explained more below. The present system is especially adapted to determine low levels of retardance. Low retardance levels are determined with a sensitivity of less than ±0.01 nm.

In order to obtain an unambiguous measure of the sample-induced retardance, the beam "Bi" that passes out of the sample is separated into two parts having different polarization directions and thereby defining two channels of information for subsequent processing.

Turning first to the preferred mechanism for separating the beam "Bi," there is located in the path of that beam (hereafter referred to as the incidence path) a beam-splitting mirror 30. Part "B1" of the beam "Bi" passes completely through the beam-splitting mirror 30 and enters a detector assembly 32 for detection.

FIG. 3 depicts a preferred mechanism for supporting the beam-splitting mirror 30. In particular, the mirror 30 is seated in the central aperture of a housing 31 that is rigidly supported by an arm 33 to a stationary vertical post 36. The post 36 is employed for supporting all of the optical components of the system so that the paths of the light are generally vertical.

The diameter of the mirror 30 is slightly less than the diameter of the housing aperture. The aperture is threaded except for an annular shoulder that projects into the lowermost end of the aperture to support the periphery of the flat, round mirror 30. A retainer ring 40 is threaded into the aperture to keep the mirror in place in the housing 31 against the shoulder.

In a preferred embodiment, care is taken to select and mount the mirror 30 so that substantially no stress-induced birefringence is introduced into the mirror. In this regard, the mirror is preferably made of Schott Glass type SF-57 glass. This glass has an extremely low (near zero) stress-optic coefficient. The retainer ring 40 is carefully placed to secure the mirror without stressing the glass. Alternatively, flexible adhesive may be employed to fasten the mirror. No set-screws or other stress-inducing mechanisms are employed in mounting the mirror.

It is noteworthy here that, although a beam-splitting mirror is preferred, one can substitute other mechanisms (such as a flipper mirror arrangement) for separating the beam "Bi" into two parts.

The part of the beam "B1" that passes through the mirror 30 enters the detector assembly 32 (FIG. 1), which includes a compact, Glan-Taylor type analyzer 42 that is arranged such that its polarization direction is at −45° from the baseline axis. From the analyzer 42, the beam "B1" enters a detector 44, the particulars of which are described more below.

The reflective surface 35 of the beam-splitting mirror 30 (FIG. 3) faces upwardly, toward the sample 26. The mirror is mounted so that the incidence path (that is, the optical path of the beam "Bi" propagating from the sample 26) is nearly normal to the reflective surface 35. This orientation is preferred for substantially eliminating retardance that would otherwise be introduced by an optical component that is called on to redirect the path of the beam by more than a few degrees.

FIG. 1 shows as "A" the angle made between the beam "Bi" traveling along the incidence path and the beam part "Br" that is reflected from the mirror 30. Angle "A" is shown greatly enlarged for illustrative purposes. In a preferred embodiment, this angle is greater than 0° but less than 10°. Most preferred is an angle "A" of under 5°.

Figure 4:
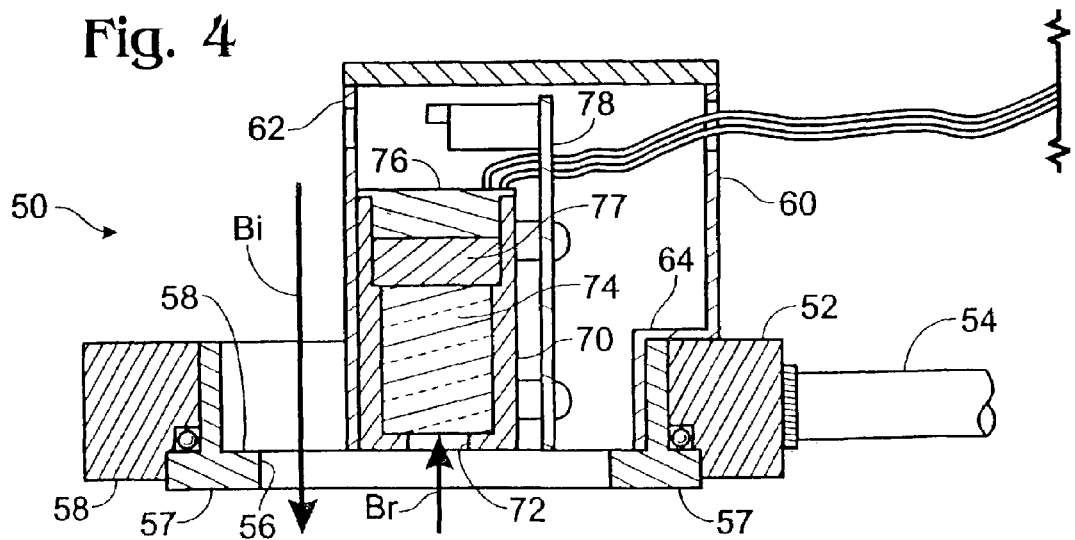
FIG. 4 is a cross-sectional view of one of the detector assemblies of the system.

The reflected part of the Beam "Br" is incident upon another detector assembly 50. That assembly 50 is mounted to the post 36 (FIG. 3) and configured in a way that permits the assembly to be adjacent to the incident beam "Bi" and located to receive the reflected beam "Br." More particularly, the assembly 50 includes a base plate 52 that is held to the post 36 by an any 54. As seen best in FIG. 4, the base plate includes an inner ring 57 that is rotatably mounted to the base plate and has a large central aperture 56 that is countersunk to define in the bottom of the plate 52 an annular shoulder 58.

The detector components are compactly integrated and contained in a housing 60 that has a flat front side 62. The remainder of the side of the housing is curved to conform to the curvature of the central aperture 56 of the base plate 52. Moreover, this portion of the housing 60 includes a stepped part 64 that permits the curved side of the housing to fit against the base plate 52 and be immovably fastened thereto.

A sub-housing 70 is fastened inside of the detector components housing 60 against the flat side 62. The sub-housing 70 is a generally cylindrical member having an aperture 72 formed in the bottom. Just above the aperture 72 resides a compact, Glan-Taylor type analyzer 74 that is arranged so that its polarization direction is 0°, parallel with that of the PEM 24.

Stacked above the analyzer 74 is a narrow-band interference filter 77 that permits passage of the polarized laser light but blocks unwanted room light from reaching a detector 76.

The detector is preferably a photodiode that is stacked above the filter. The photodiode detector 76 is the preferred detection mechanism and produces as output a current signal representative of the time varying intensity of the received laser light. With respect to this assembly 50, the laser light is that of the beam "B2," which is the reflected part "Br" of the beam that propagated through the sample 26.

The photodiode output is delivered to a preamplifier carried on an associated printed circuit board 78 that is mounted in the housing 60. The preamplifier 75 (FIG. 2) provides output to a phase sensitive device (preferably a lock-in amplifier 80) in the form of a low-impedance intensity signal $V_{AC}$, and a DC intensity signal $V_{DC}$, which represents the time average of the detector signal.

It is noteworthy here that the other detector assembly 32 (FIG. 3) to which is directed the non-reflected part "B1" of the beam "Bi" is, except in two respects, the same construction as the just described assembly 50. As shown in FIG. 3, the detector assembly 32 is mounted to the post 36 in an orientation that is generally inverted relative to that of the other detector assembly 50. Moreover, the analyzer 42 of that assembly 32 is arranged so that its polarization direction is oblique to the polarization direction of the analyzer 74 in the other detector assembly 50. Specifically, the analyzer 42 is positioned with its polarization direction at −45°. The preferred analyzer position is established by rotating the detector assembly via the inner ring 57 discussed above.

The photodiode of detector assembly 32 produces as output a current signal representative of the time varying intensity of the received laser light. With respect to this assembly 32, the laser light is that of the beam "B1," which is the non-reflected part of the beam "Bi" that propagated through the sample 26.

The photodiode output of the detector assembly 32 is delivered to a preamplifier 79, which provides its output to the lock-in amplifier 80 (FIG. 2) in the form of a low-impedance intensity signal $V_{AC}$, and a DC intensity signal $V_{DC}$, which represents the time average of the detector signal.

In summary, the lock-in amplifier 80 is provided with two channels of input: channel 1 corresponding to the output of detector assembly 32, and channel 2 corresponding to the output of detector assembly 50. The intensity information received by the lock-in amplifier on channel 1— because of the arrangement of the −45° analyzer 42—relates to the 0° or 90° component of the retardance induced by the sample 26. The intensity information received on channel 2 of the lock-in amplifier 80—as a result of the arrangement of the 0° analyzer 74—relates to the 45° or −45° component of the retardance induced by the sample. As explained below, this information is combined in an algorithm that yields an unambiguous determination of the magnitude of the overall retardance induced in the sample (or a location on the sample) as well as the orientation of the fast axis of the sample (or a location on the sample).

The lock-in amplifier 80 may be one such as manufactured by EG&G Inc., of Wellesley, Mass., as model number 7265. The lock-in amplifier takes as its reference signal 82 the oscillation frequency applied by the PEM controller 84 to the transducers 29 that drive the optical element 25 of the PEM 24. The lock-in amplifier 80 communicates with a digital computer 90 via an RS232 serial interface.

For a particular retardance measurement, such as one taken during the scanning of several locations on a sample, the computer 90 obtains the values of channel 1. The computer next obtains the values of channel 2. The intensity signals on the detectors in channels 1 and 2 are derived as follows:

$$I_{ch1} = 1 + \cos(4\rho)\sin^2\left[\frac{\delta}{2}\right]\cos\Delta - \cos^2\left[\frac{\delta}{2}\right]\cos\Delta + \cos(2\rho)\sin\delta\sin\Delta \quad \text{Eqn. (1)}$$

$$I_{ch2} = 1 + \sin(4\rho)\sin^2\left[\frac{\delta}{2}\right]\cos\Delta + \sin(2\rho)\sin\delta\sin\Delta$$

where $\Delta$ is the PEM's time varying phase retardation; $\delta$ is the magnitude of the sample's retardance; and $\rho$ is the azimuth of the fast axis of the sample's retardance.

The Mueller matrix for a linearly birefringent sample ($\delta$, $\rho$) used in the derivation has the following form:

$$\begin{bmatrix} 1 & 0 & 0 & 0 \\ 0 & \cos(4\cdot\rho)\cdot\sin\left(\frac{\delta}{2}\right)^2 + \cos\left(\frac{\delta}{2}\right)^2 & \sin(4\cdot\rho)\cdot\sin\left(\frac{\delta}{2}\right)^2 & -\sin(2\cdot\rho)\cdot\sin(\delta) \\ 0 & \sin(4\cdot\rho)\cdot\sin\left(\frac{\delta}{2}\right)^2 & -\left(\cos(4\cdot\rho)\cdot\sin\left(\frac{\delta}{2}\right)^2\right) + \cos\left(\frac{\delta}{2}\right)^2 & \cos(2\cdot\rho)\cdot\sin(\delta) \\ 0 & \sin(2\cdot\rho)\cdot\sin(\delta) & -(\cos(2\cdot\rho)\cdot\sin(\delta)) & \cos(\delta) \end{bmatrix}$$

In equations (1), $\sin \Delta$ ($\Delta = \Delta_0 \sin \omega t$, where $\omega$ is the PEM's modulating frequency; $\Delta_0$ is the maximum peak retardance of the PEM) can be expanded with the Bessel functions of the first kind:

$$\sin\Delta = \sin(\Delta_0\sin(\omega t)) = \sum_{2k+1} 2J_{2k+1}(\Delta_0)\sin((2k+1)\omega t) \quad \text{Eqn. (2)}$$

where k is either "0" or a positive integer; and $J_{2k+1}$ is the (2k+1)th order of the Bessel function. Similarly, $\cos \Delta$ can be expanded with the even harmonics of the Bessel functions:

$$\cos\Delta = \cos(\Delta_0\sin(\omega t)) \quad \text{Eqn. (3)}$$
$$= J_0(\Delta_0) + \sum_{2k} 2J_{2k}(\Delta_0)\cos((2k)\omega t)$$

where $J_0$ is the $0^{th}$ order of the Bessel function, and $J_{2k}$ is the (2k)th order of the Bessel function.

As seen from equations 1–3, it is preferable to determine the magnitude and angular orientation of retardance using the signal at the PEM's first harmonic. The useful signal for measuring linear birefringence at the PEM's 2nd harmonic is modified by $\sin^2(\delta/2)$, a value that is much smaller than $\sin \delta$. The 1F electronic signal on the detectors can be expressed in equation (4):

$$I_{ch1,1F} = \sin \delta \cos(2\rho) 2J_1(\Delta_0)\sin(\omega t)$$

$$I_{ch2,1F} = \sin \delta \sin(2\rho) 2J_1(\Delta_0)\sin(\omega t) \quad \text{Eqn. (4)}$$

As noted, the 1F signal is determined using the lock-in amplifier 80 that is referenced at the PEM's first harmonic. The lock-in amplifier will exclude the contributions from all harmonics other than 1F. The output from the lock-in amplifier 80 for the two channels is:

$$I_{ch1}(1F)\sqrt{2} = \frac{I_0}{2}\delta\cos(2\rho)2J_1(\Delta_0) \quad \text{Eqn. (5)}$$

$$I_{ch2}(1F)\sqrt{2} = \frac{I_0}{2}\delta\sin(2\rho)2J_1(\Delta_0)$$

Using the approximation of $\sin \delta \approx \delta$ for low-level linear birefringence; and $\sqrt{2}$ results from the fact that the lock-in amplifier measures the r.m.s. of the signal, instead of the amplitude.

All terms appearing at a frequency other than the PEM's first harmonic are neglected in obtaining equations (5). The validity of equations (5) for obtaining the 1F $V_{AC}$ signal is further ensured from the approximation that $\sin^2(\delta/2) \approx 0$ when $\delta$ is small. This applies for low-level retardance of, for example, less than 20 nm.

In order to eliminate the effect for intensity fluctuation of the light source, or variations in transmission due to absorption, reflection losses, or scattering, the ratio of the 1F VAC signal to the VDC signal is used. (Alternatively, similar techniques can be employed, such as dynamically normalizing the DC signal to unity.) Exclusion of the cos $\Delta$ terms in equation (1) can severely affect the VDC signal in channel 1 even though it has a minimal effect on the determination of the 1F VAC signal using a high quality lock-in amplifier. The DC term of channel 1 depends on $J_0(\Delta_0)$ as seen from equation (6).

$$I_{dc1} = \frac{I_0}{2}(1 - J_0(\Delta_0)) \quad \text{Eqn. (6)}$$

$$I_{dc2} = \frac{I_0}{2}.$$

Consequently, this DC term should be corrected as in equation (7):

$$\frac{I_{ch1}(1F)}{I_{dc1}} \cdot \frac{1 - J_0(\Delta_0)}{2J_1(\Delta_0)} \cdot \sqrt{2} = R_{ch1} = \delta\cos(2\rho) \quad \text{Eqn. (7)}$$

$$\frac{I_{ch2}(1F)}{I_{dc2}} \cdot \frac{1}{2J_1(\Delta_0)} \cdot \sqrt{2} = R_{ch2} = \delta\sin(2\rho)$$

where $R_{ch1}$ and $R_{ch2}$ are experimentally determined quantities from the two channels.

To correct the "DC" term caused by the cos $\Delta$ term in channel 1, one properly sets the PEM retardation so that $J_0(\Delta_0)=0$ (when $\Delta_0=2.405$ radians, or 0.383 waves). At this PEM setting, the efficiency of the PEM for generating the 1F signal is about 90% of its maximum.

Finally, the magnitude and angular orientation of the linear birefringence is expressed in equations (8):

$$\rho = \frac{1}{2}\tan^{-1}\left[\frac{R_{ch2}}{R_{ch1}}\right] \quad \text{or} \quad \rho = \frac{1}{2}ctg^{-1}\left[\frac{R_{ch1}}{R_{ch2}}\right] \qquad \text{Eqn. (8)}$$

$$\delta = \sqrt{(R_{ch1})^2 + (R_{ch2})^2}$$

These equations (8) are compiled in a program running on the computer 90 and used to determine the magnitude and orientation of the retardance at any selected point on the sample.

Equations (8) are specifically developed for small linear birefringence. The approximation of $\sin\delta \approx \delta$ used in deriving equations (8) has an error of ~1% for $\delta=20$ nm when the light wavelength is at 632.8 nm. For any larger retardance, $\sin\delta$ should be used, instead of $\delta$.

As noted above, best retardance measurement results are achieved when one minimizes the residual birefringence present in the optical components of the system. To this end, the present system employs a PEM 24 (FIG. 5) that is specially configured to eliminate residual birefringence that may be attributable to supporting the optical element 25 of the PEM in the housing 27 (shown in dashed lines of FIG. 5). The bar-shaped optical element is bonded at each end to a transducer 29. Each transducer 29 is mounted to the PEM housing 27, as by Supports 23, so that the optical element is essentially suspended, thus free (roll any residual birefringence that may be attributable to directly mounting the oscillating optical element 25 to the PEM housing 27.

Notwithstanding efforts such as the foregoing to eliminate residual birefringence in the system components, the presence of at least some level of residual birefringence is inevitable. In the present system, highly accurate results are obtained by correcting the results of equations 8 to account for any remaining residual birefringence in the system, which residual may be referred to as the system offset. In practice, residual birefringence in the optical element of the photoelastic modulator and in the beam-splitting mirror substrate can induce errors in the resulting measurements. Any such errors can be measured by first operating the system with no sample in place. A correction for the errors is made by subtracting the error values for each channel.

The system offset is obtained by making a measurement without a sample in place. The results from both channels 1 and 2 are the system offsets at 0° and 45° respectively:

$$R^0_{ch1} = \frac{I^0_{ch1}(1F)}{2J_1(\Delta_0)I^0_{dc1}} = \delta^0 \quad (\rho = 0) \qquad \text{Eqn. (9)}$$

$$R^0_{ch2} = \frac{I^0_{ch2}(1F)}{2J_1(\Delta_0)I^0_{dc2}} = \delta^0 \quad \left(\rho = \frac{\pi}{4}\right)$$

where the superscript "0" indicates the absence of a sample. The equation bearing the term $\rho=0$ corresponds to channel 1 (the −45° analyzer 42). The equation bearing the term $\rho=\pi/4$ corresponds to channel 2 (the 0° analyzer 74). The system offsets are corrected for both channels when a sample is measured. The system offsets for channels 1 and 2 are constants (within the measurement error) at a fixed instrumental configuration. Barring any changes in the components of the system, or in ambient pressure or temperature, the system should remain calibrated.

In principle, this procedure will provide a method of self-calibration of the system. It is, however, prudent to compare the system measurement of a sample with the measurement obtained using other methods.

One such calibration sample may be provided by a compound zero-order waveplate. The compound waveplate comprises two multiple-order waveplates (e.g., quartz) or two zero-order waveplates (e.g., mica) selected to have a very small retardance difference between them (e.g., less than 0.03 wavelengths). They would be combined with their axes at right angles so that the retardance of one is subtracted from the other to produce the sought-after low-level retardance, compound zero-order waveplate(s) for use in calibration. Such a configuration will provide a uniform retardance across the surface with a low temperature coefficient of retardance.

If the components of the present system are correctly set up, the magnitude of the measured, sample-induced retardance will be independent of the sample's angular orientation. This angular independence may be lost if: (1) the polarization directions of the polarizer 22 and analyzers 42, 74 are not precisely established, and (2) the maximum peak retardance of the PEM is not precisely calibrated. What follows is a description of correction techniques for eliminating the just mentioned two sources of possible "angular dependence" errors.

As respects the precise establishment of the polarization directions of the polarizer 22 and analyzers 42, 74, the correction technique applied to the polarizer 22 involves the following steps:

1. With the PEM operating, approximately orient the polarizer 22 and the channel 1 analyzer/detector assembly 32 at 45° and −45°, respectively.
2. Rotate the polarizer 22 in fine increments while monitoring the 2F (100 kHz) lock-in amplifier signal from channel 1. When the 2F signal reaches "0" (practically, the noise level at the highest lock-in amplifier sensitivity possible), read precisely the angle on the polarizer rotator.
3. Rotate the polarizer 22 by precisely 45°, which is the correct position for the polarizer.
4. Once the position of the polarizer 22 is correctly established, turn off the PEM and rotate analyzer/detector assembly 32 while monitoring the lock-in amplifier's $V_{DC}$ signal from channel 1. When the minimum $V_{DC}$ signal is achieved, the position of analyzer/detector assembly 32 is set correctly.
5. Once the position of the polarizer 22 is correctly established, rotate analyzer/detector assembly 50 while monitoring the lock-in amplifier's 2F (100 kHz) signal from channel 2. When this 2F signal reaches "0" (practically, the noise level at the highest lock-in amplifier sensitivity possible), the position of analyzer/detector assembly 50 is set correctly.

As respects the calibration of the PEM, the following technique may be employed:

1. Set the channel 1 analyzer/detector assembly 32 at −45° when the polarizer 22 is at +45°.
2. Record the $V_{DC}$ signals with a precision voltmeter while the PEM retardance is changed in the vicinity of, for example, ±10% of the selected peak retardance of the PEM.
3. Set the channel 1 analyzer/detector assembly 32 at +45°.
4. Record $V_{DC}$ signals with a precision voltmeter while the PEM retardance is changed in the selected vicinity.

5. Plot the two $V_{DC}$ curves against PEM retardation around the selected peak retardance. The intersection of the two curves is the retardance for $J_0=0$.
6. Set the PEM retardance value at the intersection value of step 5.

As mentioned above, the motion controllers of the sample stage 28 are controlled in a conventional manner to incrementally move the sample 26 about orthogonal (X, Y) axes, thereby to facilitate a plurality of measurements across the area of a sample. The spatial resolution of these measurements can be established as desired (e.g., 3.0 mm), provided that the sought-after resolution is not finer than the cross section of the beam that strikes the sample. In this regard, the cross sectional area or "spot size" of the laser beam may be minimized, if necessary, by the precise placement of a convex lens with an appropriate focal length, such as shown as line 96 in FIG. 1, between the light source 20 and the polarizer 22. The lens could be, for example, removably mounted to the top of the polarizer 22. The lens 96 would be in place in instances where a very small spot size of, for example, 0.1 mm (and corresponding spatial resolution) is desired for a particular sample.

In some instances it may be desirable to enlarge the spot size provided by the laser source. To this end a lens or lens system such as provided by a conventional beam expander may be introduced into the system between the laser 20 and the polarizer 22.

Figure 6:
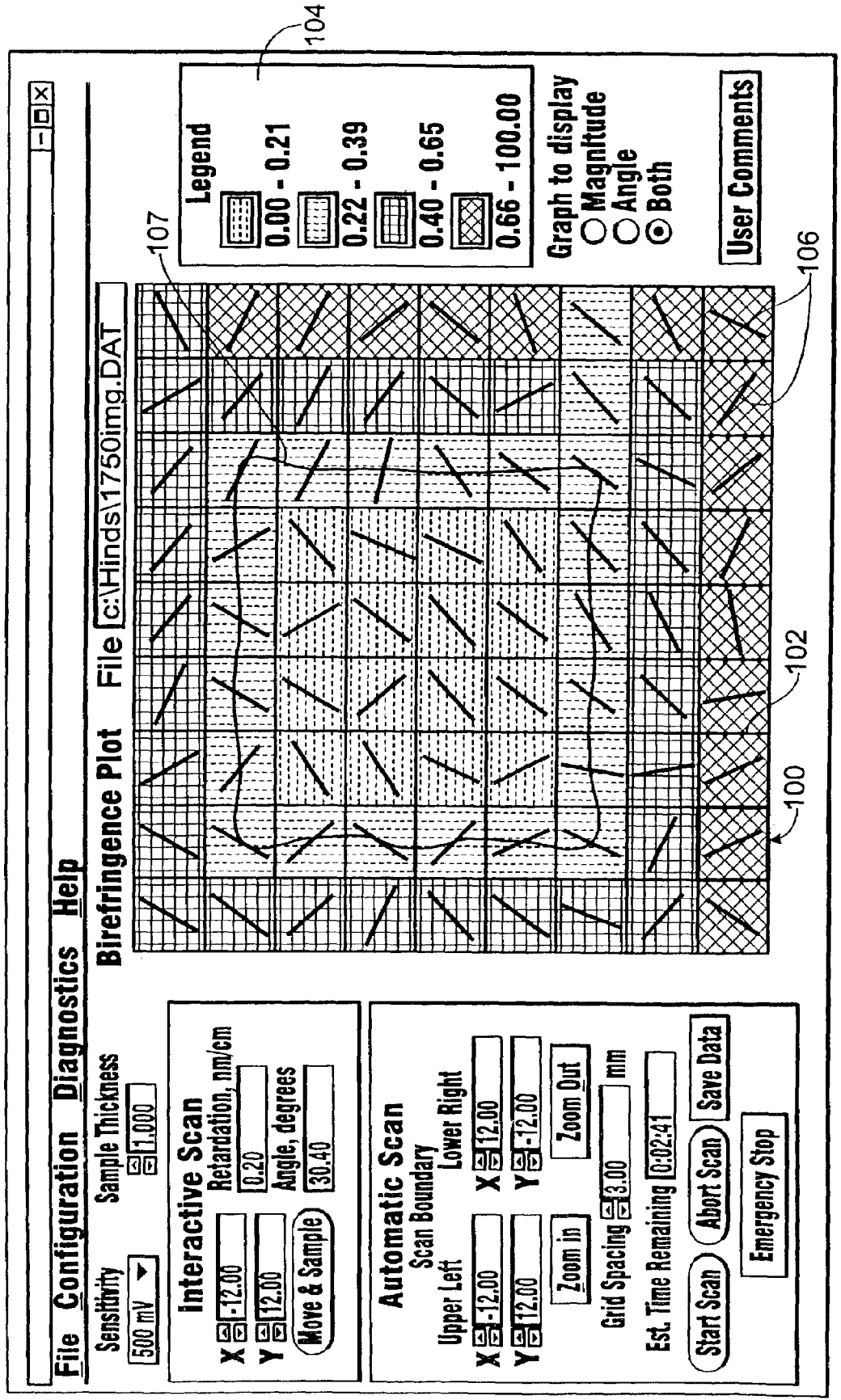
FIG. 6 is a drawing depicting a graphical display provided by the system of the present invention.

The measured retardance values can be handled in a number of ways. In a preferred embodiment the data collected from the multiple scans of a sample are stored in a data file and displayed as a plot on a computer display 92. One such plot 100 is shown in FIG. 6. Each cell 102 in a grid of cells in the plot indicates a discrete location on the sample. The magnitude of the retardance is depicted by color coding. Here different shadings in the cells represent different colors. In FIG. 6, only a few different colors and cells are displayed for clarity. It will be appreciated, however, that a multitude of cells can be displayed. The legend 104 on the display correlates the colors (the color shading is omitted from the legend) to a selectable range of retardance values within which the particular measurement associated with a cell 102 falls. A line 106 located in each cell 102 extends across the center of each cell and presents an unambiguous visual indication of the full physical range (−90° to +90°) of the orientation of the fast axis of the sample at each sampled location. Thus, the orientation of the fast axis and the retardance magnitude measurements are simultaneously, graphically displayed for each location. With such a complete, graphical display, an inexperienced operator user is less likely to make errors in analyzing the data that are presented.

In a preferred embodiment, the just described retardance measurements are displayed for each cell as soon as that cell's information is computed. As a result of this instantaneous display approach, the operator observes the retardance value of each cell, without the need to wait until the retardance values of all of the cells in the sample have been calculated. This is advantageous for maximizing throughput in instances where, for example, an operator is charged with rejecting a sample if the birefringence value of any part of the sample exceeds an established threshold.

Also illustrated in FIG. 6 is a contour line placed there as an example of a contour line that follows a common measured range of retardance magnitude. For simplicity, only a single one of several contour lines is shown for the low-resolution plot of FIG. 6.

It will be appreciated that any of a number of variations for displaying the measured data will suffice. It will also be apparent from FIG. 6 that the means for setting parameters of how the sample is scanned (scan boundaries, grid spacing sample thickness, etc.) and the resulting data are conveniently, interactively displayed.

Another approach to graphically displaying the retardance magnitude and orientation information provided by the present system is to depict the retardance magnitude for a plurality of locations in a sample via corresponding areas on a three-dimensional contour map. The associated orientations are simultaneously shown as lines or colors in corresponding cells in a planar projection of the three dimensional map.

FIG. 7 depicts an arrangement for measuring retardance magnitude and orientation in a sample 124 that is reflectively coated on one side. Apart from the different sample 124 and the relative locations of the optical components, the components of the system of FIG. 7 match those of the embodiment of FIG. 1 and thus carry the same reference numbers, with a few exceptions as noted below.

The sample 124 (FIG. 7) is coated on one side with a reflective surface, such as very thin layer of chromium. The sample is placed on the sample stage with the coated surface on the bottom. The beam "B" is directed to pass through the sample 124. The sample stage is slightly tilted (or, alternatively, the sample is secured in a tilted holder mounted to a flat stage) so that the beam reflects from the coated surface toward the beam-splitting mirror 30 and detector assembly 32, which are, in this embodiment, supported above the sample stage 28 as shown. Preferably, these components are located as near as practical to the beam "B" so that the beam "Bi" reflected from the sample 124 is angled "R" only slightly away (for example 2° to 5°) from the beam "B" propagating from the PEM 24. The beam reflected by the sample (as distinguished from the beam "Br" reflected by the mirror 30) corresponds, from a processing standpoint, to the beam "Bi" impinging on the mirror 30 of the FIG. 1 embodiment. Thus, the processing of the two beam parts "B1" and "B2" are the same for both embodiments. Of course, the measured retardance magnitude of the sample 124 will necessarily comprise two passes of the beam through the sample. Therefore the measured value will be divided by two.

As noted above, it is desirable to locate the beam-splitting mirror 30 as near as practical to the beam "B" so that the beam "Bi" reflected from the sample 124 is angled "R" only slightly away (for example 2° to 5°) from the beam "B" propagating from the PEM 24. To this end, the housing 31 may be modified to support a mirror that is semi-circular in shape such that the flat edge of the mirror is located adjacent to the beam "B." The beam "Bi", therefore, could be reflected to a location on the mirror that is very close to that edge, hence to the beam "B" as desired.

While the present invention has been described in terms of preferred embodiments, it will be appreciated by one of ordinary skill in the art that modifications may be made without departing from the teachings and spirit of the foregoing. For example a second lock-in amplifier may be employed (on for each channel) for increasing the speed with which data is provided to the computer.

Also, one of ordinary skill will appreciate that sequential measurement using a single detector may be employed for measuring the intensity signal in two different polarization directions and thereby defining two channels of information for subsequent processing. For example, a single detector assembly could be employed. This dispenses with the second detector assembly and the beam-splitter mirror. Such a set-up, however, would require either rotating the analyzer or switching between two polarizers of different orientations to ensure unambiguous retardance measurements and to ascertain the orientation of the fast axis. Alternatively, the sample and the analyzer may be rotated by 45°.

The preferred embodiment of the present invention uses a HeNe laser for a stable, pure, monochromatic light source. The HeNe laser produces a beam having a 632.8 nm wavelength. In some instances, retardance magnitude measurements using light sources having other frequencies are desired.

As another aspect of the present invention, one can develop and apply correction factors to convert the retardance magnitude measurement of the sample as measured by the HeNe laser to the retardance value that would occur in the sample at another source-light wavelength. In this regard, FIG. 8 charts experimental results showing the oscillation amplitude required to produce, via the PEM, a selected peak retardation (such as half-wave) plotted against different source wavelengths for a PEM that employs a fused silica type optical element.

Figure 8:
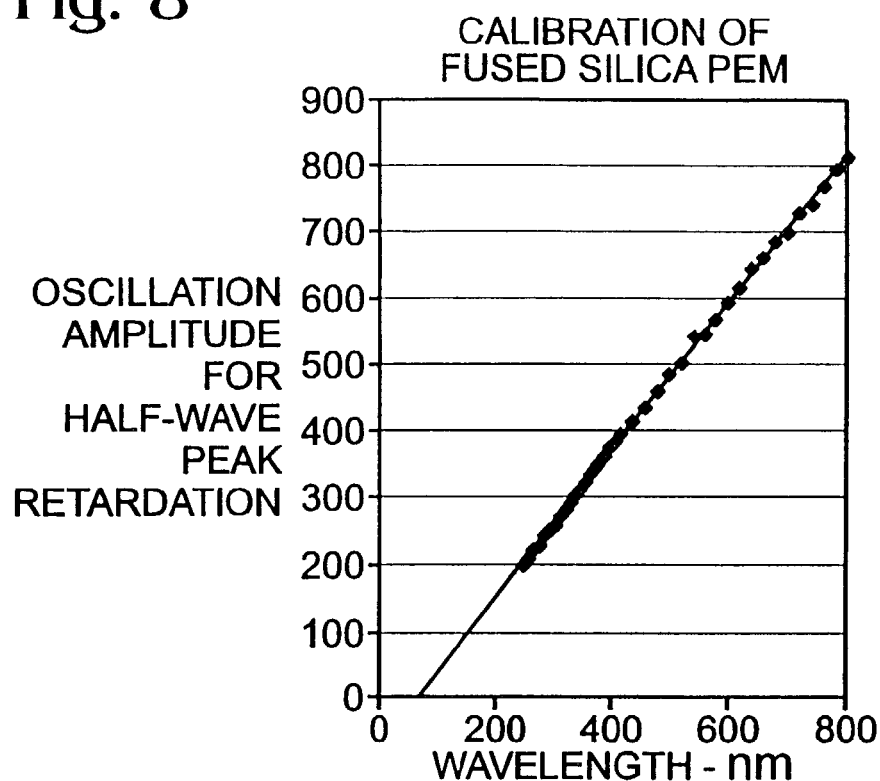
FIG. 8 is a graph that plots, for a selected retardance, the oscillation amplitude of the polarization modulator against a number of source-light wavelengths, for a polarization modulator that employs a preferred type of optical element.
Figure 9:
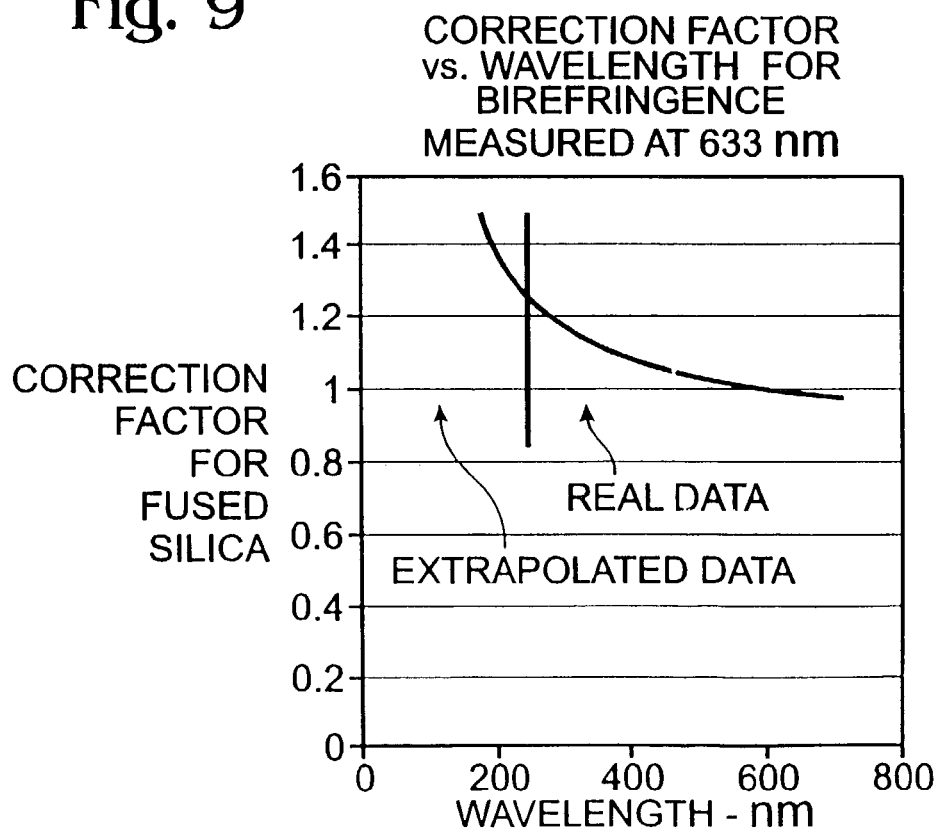
FIG. 9 is a graph, based in part on the data shown in FIG. 8, that represents a correction factor that may be applied to convert the retardance value of an optical-material sample as measured at one source-light wavelength to the retardance value that would occur in the sample at another source-light wavelength.

FIG. 9 is developed by using, in part, the plot of FIG. 8 to produce a curve that represents a correction factor that is applied to the retardance magnitude value of the sample as measured at one wavelength (such as the 632.8 nm wavelength of the HeNe laser), thereby to arrive at (either directly or by extrapolation) the retardance magnitude that would occur in the sample at other wavelengths, such as a UV wavelength of 157 nm. The data in FIG. 9 was generated from an experiment involving a PEM having a fused silica optical element for use with samples of similar fused silica material.

The wavelength correction technique just described for fused silica can also be applied to other materials. For example, FIG. 10 charts experimental results showing the oscillation amplitude required to produce, via the PEM, a selected peak retardation (such as half-wave) plotted against different source wavelengths for a PEM that employs a calcium fluoride optical element.

Figure 10:
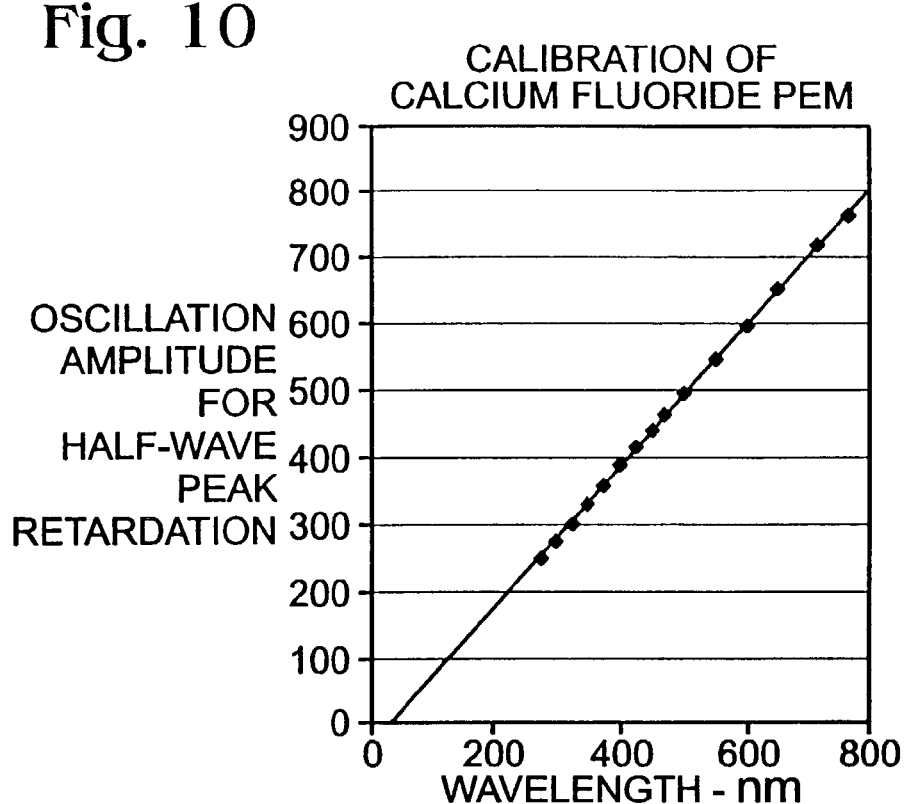
FIG. 10 is a graph that plots, for a selected retardance, the oscillation amplitude of the polarization modulator against a number of source-light wavelengths, for a polarization modulator that employs an alternative type of optical element.
Figure 11:
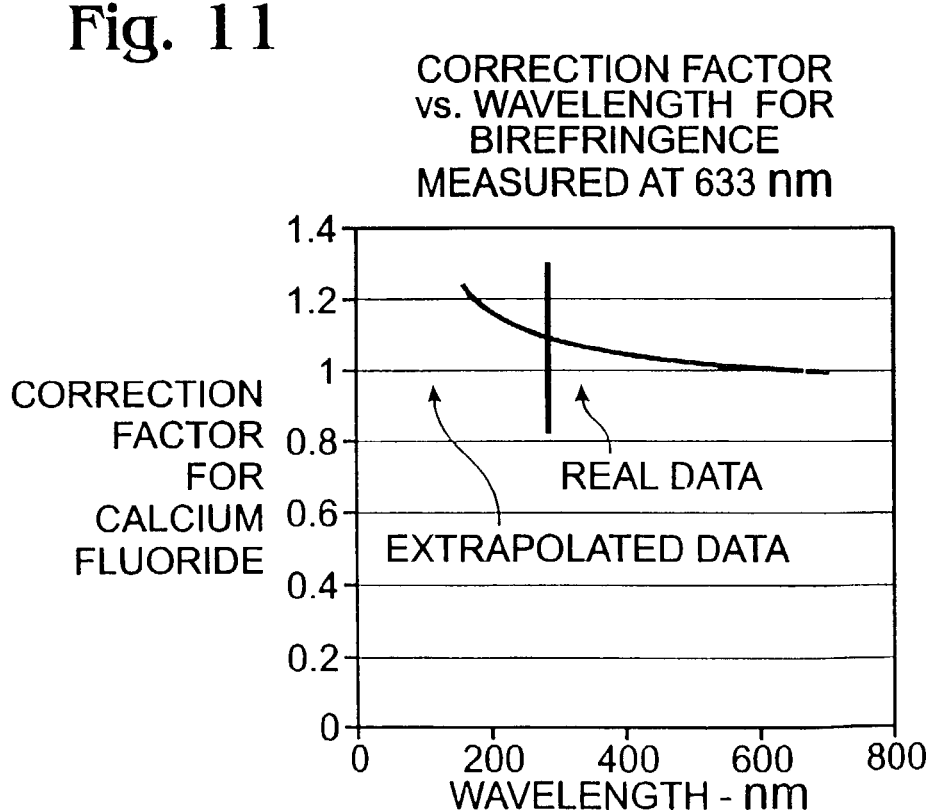
FIG. 11 is a another graph, like FIG. 9, that represents a correction factor that may be applied to convert the retardance value of an optical-material sample as measured at one source-light wavelength to the retardance value that would occur in the sample at another source-light wavelength.

FIG. 11 is developed by using the plot of FIG. 10 to produce a curve that represents a correction factor that is applied to the retardance magnitude as measured at one wavelength (such as the 633 nm wavelength of the HeNe laser), thereby to arrive at (either directly or by extrapolation) the retardance magnitude that would occur in the sample at other wavelengths, such as a UV wavelength of 157 nm. The data in FIG. 11 was generated from an experiment involving a PEM having a calcium fluoride optical element for use with samples of similar calcium fluoride material.

As another approach to correcting the measured retardation magnitude at one source-light wavelength to relate to the retardance magnitude at another wavelength, one can refer to the stress-optic coefficient of the sample material being tested, which coefficient is known as a function of wavelength. The retardance magnitudes measured at two different wavelengths are directly proportional to the stress-optic coefficient of the material.

Circular Retardance Measurement

As noted above with respect to FIGS. 1 and 7, the samples 26, 127 will induce retardance into the light beam that passes through it. In some instances the retardance is induced in the beam by a sample (as, for example, chiral media) having circular birefringence. The resultant retardance value (hereafter referred to as ("circular retardance"), in addition to the value resulting from the linear birefringence discussed above, is also determined in accordance with the processing provided by the present invention, as explained more below. The present system is especially adapted to determine low levels of circular retardance. Low retardance levels are determined with a sensitivity of about $\pm 1 \times 10^{-5}$ radians.

Figure 2:
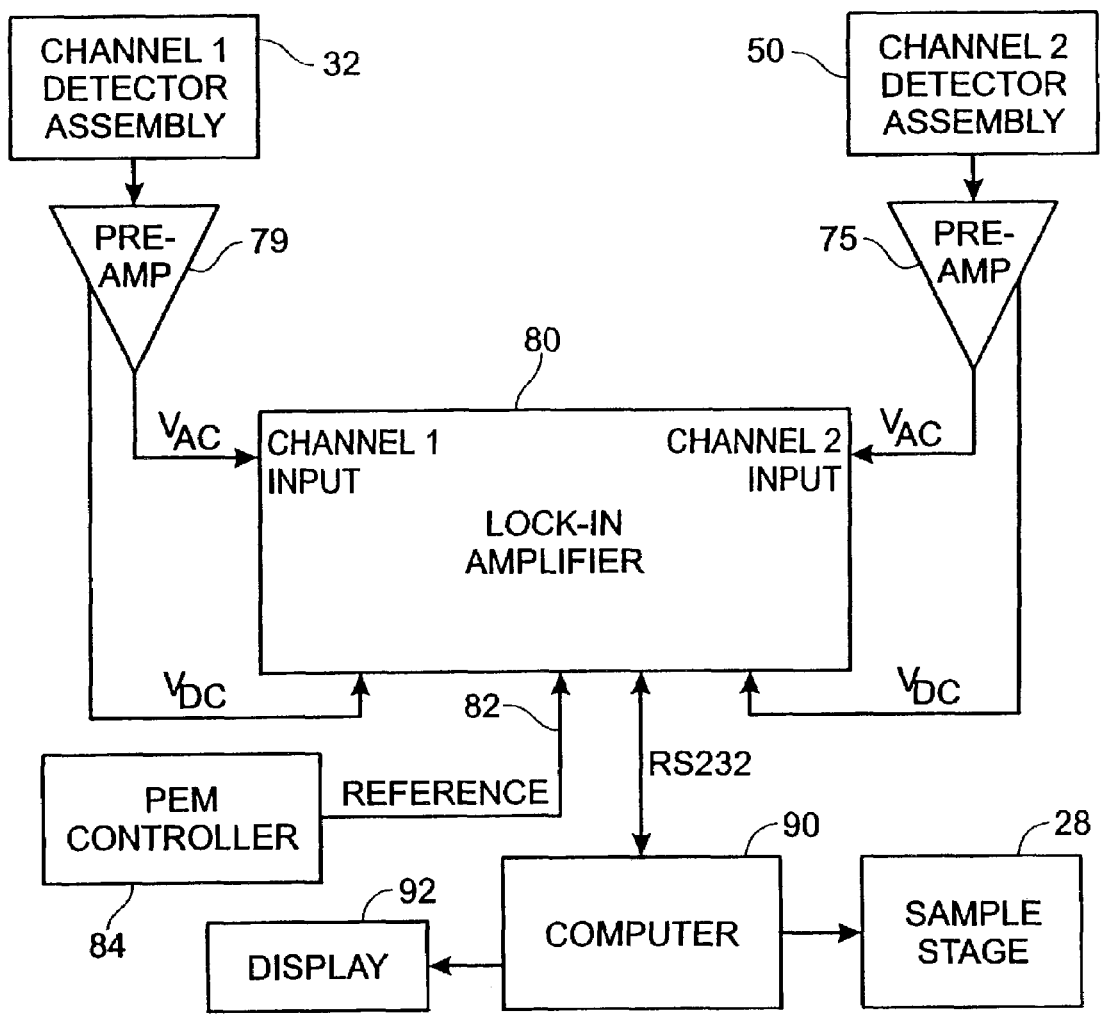
FIG. 2 is a block diagram of the processing components of the present system illustrating the processing of linear birefringence.
Figure 12:
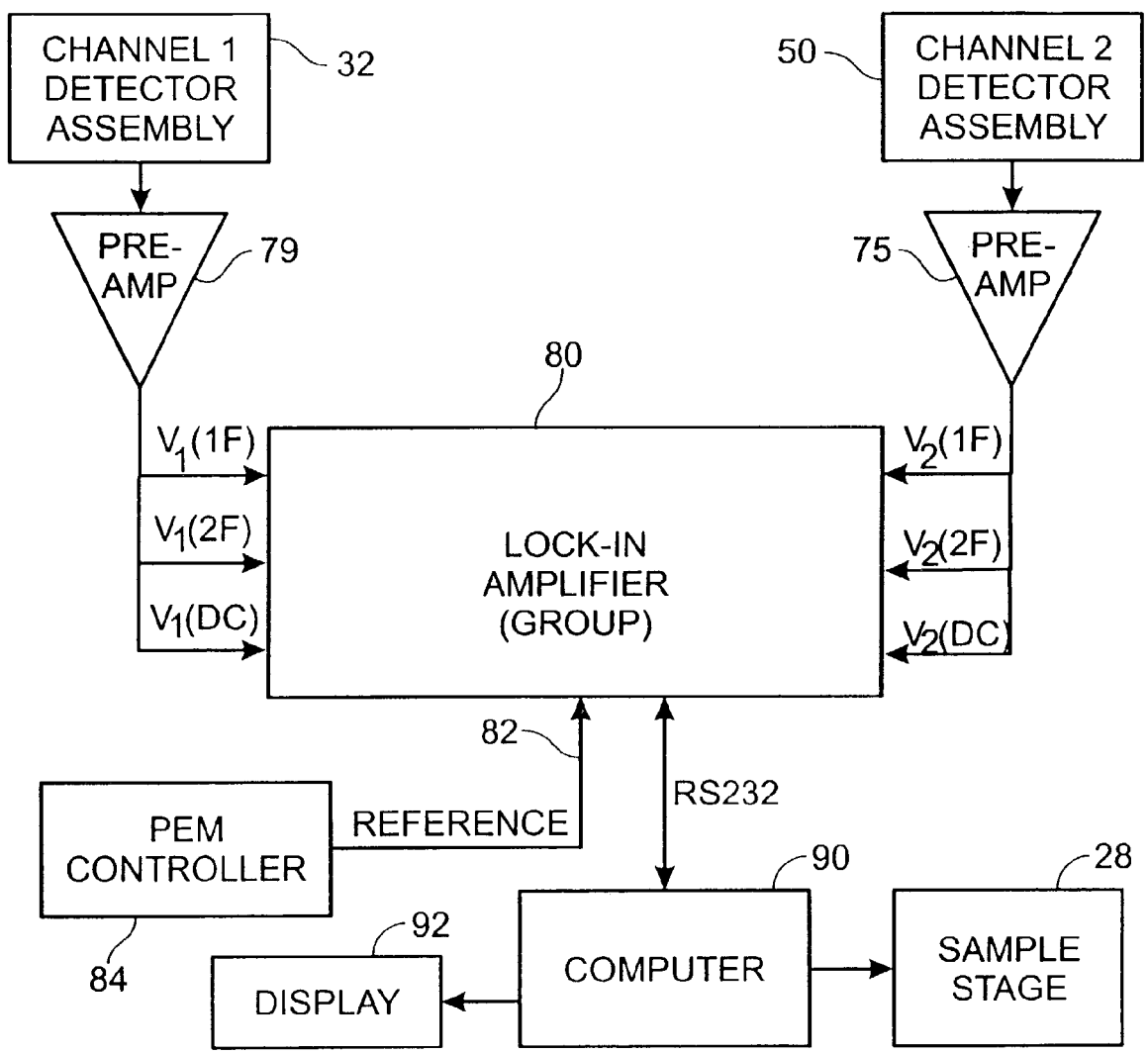
FIG. 12 is a block diagram of the processing components of the present system illustrating the processing of circular birefringence.

The determination of the circular retardance employs, in a preferred embodiment, the optical components arrangement shown in the diagram of FIG. 1. This preferred embodiment also employs the same processing components as depicted in FIG. 2, which also appear in FIG. 12. FIG. 12 is a modification of the diagram of FIG. 2 for describing the particular signal processing aspects of this embodiment of the invention.

The signal presented by the channel 2 detector assembly 50 (FIG. 12) is preferred for determining circular retardance. Using Mueller matrix calculus, signals in channel two can be derived as follows:

$$\begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot \begin{bmatrix} 1 & 0 & 0 & 0 \\ 0 & \cos\alpha & \sin\alpha & 0 \\ 0 & -\sin\alpha & \cos\alpha & 0 \\ 0 & 0 & 0 & 1 \end{bmatrix} \cdot \begin{bmatrix} 1 & 0 & 0 & 0 \\ 0 & 1 & 0 & 0 \\ 0 & 0 & \cos\Delta & \sin\Delta \\ 0 & 0 & -\sin\Delta & \cos \end{bmatrix} \cdot \begin{bmatrix} 1 \\ 0 \\ 1 \\ 0 \end{bmatrix} \rightarrow \begin{bmatrix} 1 + \sin\alpha \cdot \cos\Delta \\ 1 + \sin\alpha \cdot \cos\Delta \\ 0 \\ 0 \end{bmatrix}$$

where $\Delta$ is the PEM's time varying phase retardation ($\Delta = \Delta_0 \sin \omega t$, where $\omega$ is the PEM's modulating frequency; $\Delta_0$ is the retardation amplitude of the PEM), and $\alpha$ is the magnitude of the circular retardance.

The light intensity signals at the detector for channel II are:

$$I_{ch2} = \frac{I_0}{2} \{1 + \sin(\alpha) \cos\Delta\} \qquad \text{Eqn. (10)}$$

where $I_0$ is the light intensity after the first polarizer.

The function of $\cos \Delta$ in equation 10 can be expanded with the Bessel functions of the first kind:

$$\cos\Delta = \cos(\Delta_0 \sin(\omega t)) = J_0(\Delta_0) + \sum_{2k} 2J_{2k}(\Delta_0)\cos((2k)\omega t) \qquad \text{Eqn. (11)}$$

where $J_0$ is the 0th order of the Bessel function, and $J_{2k}$ is the (2k)th order of the Bessel function.

Substituting equation (11) into equation (10) and taking only up to the second order of the Bessel functions, we obtain:

$$I_{ch2} = \frac{I_0}{2}\{1 + J_0(\Delta_0)\sin(\alpha) + 2J_2(\Delta_0)\sin(\alpha)\cos(2\omega t) + \ldots\} \quad \text{Eqn. (12)}$$

As seen from equation 12, the detector signal of channel II contains "DC" terms, a 2F ($\cos(2\omega t)$) term and higher order harmonic terms. It is the 2F "AC" signal that is most useful for determining the circular birefringence. The 2F "AC" signal can be determined using a lock-in amplifier 80 that is referenced at the PEM's second harmonic frequency. For theoretical evaluation, we assume that a perfect lock-in amplifier will exclude the contributions from all other harmonics. The 2F signal measured by the lock-in amplifier for channel II is:

$$V_{ch2}(2F) = \frac{K_{Ch2}}{\sqrt{2}} \frac{I_0}{\sqrt{2}} \alpha 2J_2(\Delta_0) \quad \text{Eqn. (13)}$$

where we have used $V_{Ch2}=K_{Ch2}I_{Ch2}$ ($V_{Ch2}$ is the detector's electronic signal and $K_{Ch2}$ is an instrumental constant), and the small angle approximations (sin $\alpha = \alpha$); and $\sqrt{2}$ results from the fact that the output of a lock-in amplifier measures the root-mean-square, not the signal amplitude.

The "DC" signals for channel II can be derived from equation (12).

$$DC_{ch2} = \frac{K_{ch2}I_0}{2}(1 + \sin\alpha J_0(\Delta_0)) \quad \text{Eqn. (14)}$$

When the PEM retardation amplitude $\Delta_0$=2.405 radians (0.3828 waves) is chosen, $J_0(\Delta_0)$=0. At this PEM setting, the 2F signal and the "DC" terms for channel II are:

$$V_{ch2}(2F) = \frac{K_{Ch2}}{\sqrt{2}} \frac{I_0}{2} \alpha 2J_2(\Delta_0) \quad \text{Eqn. (15)}$$

$$DC_{ch2} = \frac{K_{Ch2}I_0}{2}$$

In order to eliminate the effect of light intensity variations due to light source fluctuations and the absorption, reflection and scattering from the sample and other optical components, the ratio of the 2F "AC" signal to the "DC" signal is used. The ratios of "AC" signal to the "DC" signal for both channels are represented in equation (16):

$$\frac{V_{ch2}(2F)}{DC_{ch2}} = \sqrt{2}\, J_2(\Delta_0)\alpha \quad \text{Eqn. (16)}$$

Finally, the circular birefringence of the sample is expressed as:

$$\alpha = \frac{V_{ch2}(2F)}{DC_{ch2}} \cdot \frac{1}{\sqrt{2}\, J_2(\Delta_0)} \quad \text{Eqn. (17)}$$

here $\alpha$, represented in radians, is a scalar that can be converted to degrees.

The mathematical sign of the $\alpha$ term calculated above is indicative of the direction of rotation of the polarization plane of the beam. For instance a positive value indicates rotation in the right-hand sense; negative meaning rotation in the left-hand sense.

A single lock-in amplifier 80 (FIG. 12) will suffice for allowing sequential data collection (alternating between channel 1 and channel 2) while the beam B is directed through a single location on the sample. As a result, the linear retardance value $\delta$ and the circular retardance $\alpha$ may be substantially simultaneously determined for any given sample.

As indicated in FIG. 12, a group of lock-in amplifiers may be employed for providing to the computer 90 simultaneously received signals from both channel 1 and channel 2, thereby reducing the overall time required for simultaneously processing of the linear and circular retardance values for a given location.

It will be appreciated that the various refinements described above with respect to the elimination of residual birefringence in the PEM and system offsets are applicable irrespective of whether linear retardance, circular retardance, or both are determined.

Similarly, the calibration techniques described above are also applicable when the system is used for calculating circular retardance. Moreover, it is contemplated that, depending on the characteristics of the sample, different light source frequencies (that is, other than the preferred 632.8 nm wavelength HeNe laser) may be desirable.

It will also be appreciated that the magnitude and rotation direction of each circular retardance measurement can be stored and displayed in a manner as described above with respect to linear retardance magnitude and angle (See FIG. 6). In one preferred embodiment, the display features the simultaneous display (using two windows) of the detected linear and circular retardance values.

In some instances it may be desirable to determine the circular retardance of a sample having a reflective coating. Thus, the arrangement of optical components described above with respect to FIG. 7 may be employed (allowing, as an option, the simultaneous determination of the linear retardance of the same sample).

It is also contemplated that the $V_1 2F$ signal transmitted on channel 1 (FIG. 12) may be measured for a determination of circular retardance. This is not preferred, however, because that signal also carries the sample's linear retardance information, which would interfere with the circular retardance information. Also, the determination of circular retardance, which depends on cos $\alpha$, is much less accurate when $\alpha$ is small (unless the circular retardance is very large).

The invention claimed is:

1. A method of measuring birefringence properties of a sample, comprising the steps of:
    modulating polarization of light;
    directing a beam of the modulated light through the sample along an incidence path;
    reflecting the beam from a reflective surface that is in the incidence path;
    analyzing the reflected part of the beam;
    determining the intensity of the reflected part of the beam;
    calculating a circular birefringence property of the sample based on the determined intensity; and
    passing a first part of the beam through the reflective surface;
    determining the intensity of the first part of the beam; and
    calculating a linear birefringence property of the sample based on the determined intensity.

2. The method of claim 1 wherein the calculating step includes calculating the magnitude of circular retardance induced by the sample.

3. The method of claim 2 wherein the calculating step includes calculating the rotational direction of the circular retardance.

4. The method of claim 1 wherein the analyzing step includes directing the first part of the beam through a first analyzer having a first polarization direction; and directing the reflected part of the beam through a second analyzer having a second polarization direction that is oriented to be different than the polarization direction of the first analyzer.

5. The method of claim 1 including the step of providing optical system components for carrying out the modulating, directing, reflecting and determining steps; and wherein the calculating step includes the step of compensating for residual birefringence present in the optical components other than the sample.

6. The method of claim 1 wherein the directing step is preceded with the step of passing the beam through the sample along a first path and then reflecting the beam back through the sample along the incidence path.

7. The method of claim 1 including the steps of:

periodically moving the sample so that the beam is directed through a plurality of locations on the sample; and calculating either or both the circular retardance magnitude of the sample and the rotational direction of the circular retardance of the sample at each location.

8. The method of claim 1 including the step of simultaneously graphically displaying the calculated circular birefringence property and the calculated linear birefringence property.

9. The method of claim 1 wherein the step of determining the intensity of the reflected part of the beam includes supporting an intensity detector adjacent to the incident path and in the path of the reflected part of the beam, thereby to minimize the angle between the incidence path and the path of the reflected part of the beam.

10. A method of measuring birefringence properties of a sample, comprising the steps of:

modulating polarization of light;

directing a beam of the modulated light through the sample along an incidence path;

dividing the beam into two, including a first beam and a second beam; and calculating a circular birefringence property of the sample based upon the intensity of the first beam and calculating linear birefringence property of the sample based upon the intensity of the second beam.

11. The method of claim 10 including the step of simultaneously displaying the circular birefringence property of the sample and the linear birefringence property.

12. The method of claim 1 wherein the calculating step includes the step of eliminating the effect of any fluctuation in the beam intensity.

13. A system for measuring circular birefringence properties in a sample, comprising:

a source of light;

means for polarizing the light;

modulating means for modulating the polarization of the light;

a sample arranged so that a beam of the modulated light passes through the sample along an incidence path;

a beam-reflecting element arranged to reflect along a reflected path a part of the beam that passes through the sample such that the reflective path is not through the sample;

an analyzer located in the reflected path; and detection means for detecting the intensity of the reflected part of the beam, thereby to provide information suitable for calculating a circular birefringence property of the sample based on the detected intensity.

14. The system of claim 13 wherein the means for modulating the polarization of the source light comprises a photoelastic modulator.

15. The system of claim 13 wherein the beam directed to the sample has a cross sectional area, the system including a lens member located between the source and the sample for changing the cross sectional area of the beam before the beam moves through the sample.

16. The system of claim 13 wherein the light source is a HeNe laser.

* * * * *